United States Patent
Knapp, II et al.

(10) Patent No.: US 9,440,024 B2
(45) Date of Patent: Sep. 13, 2016

(54) INFUSION SET WITH ANESTHETIC COMPOUND

(75) Inventors: Keith N. Knapp, II, Warwick, NY (US); Joshua Horvath, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1007 days.

(21) Appl. No.: 13/138,265

(22) PCT Filed: Jan. 26, 2010

(86) PCT No.: PCT/US2010/000190
§ 371 (c)(1),
(2), (4) Date: Aug. 22, 2011

(87) PCT Pub. No.: WO2011/056182
PCT Pub. Date: May 12, 2011

(65) Prior Publication Data
US 2011/0313391 A1 Dec. 22, 2011

Related U.S. Application Data

(60) Provisional application No. 61/202,079, filed on Jan. 27, 2009.

(51) Int. Cl.
*A61M 5/162* (2006.01)
*A61M 5/158* (2006.01)
*A61M 5/42* (2006.01)

(52) U.S. Cl.
CPC ............ *A61M 5/158* (2013.01); *A61M 5/422* (2013.01); *A61M 2005/1581* (2013.01); *A61M 2205/0238* (2013.01); *A61M 2207/00* (2013.01)

(58) Field of Classification Search
CPC .................... A61M 5/158; A61M 2005/1581
USPC .......................................... 604/112, 263, 264
See application file for complete search history.

(56) References Cited

U.S. PATENT DOCUMENTS

| 4,605,399 A | 8/1986 | Weston et al. |
| 4,755,173 A | 7/1988 | Konopka et al. |

(Continued)

FOREIGN PATENT DOCUMENTS

| JP | 2007518478 A | 7/2007 |
| JP | 2008-212683 A | 9/2008 |

(Continued)

OTHER PUBLICATIONS

Medtronic, "Infusion Set Management Tips for Achieving Balance and Control", 2008, pp. 1-2, Medtronic, USA. http://www.medtronic-diabetes.com.au/downloads/Infusion-Set-Management-Tips.pdf.

(Continued)

*Primary Examiner* — Aarti B Berdichevsky
(74) *Attorney, Agent, or Firm* — Dickinson Wright PLLC

(57) ABSTRACT

An exemplary insulin infusion set that further provides one or more set elements including the hub, hub adhesive, fluid line tubeset, connectors, catheters and insertion needles which can be impregnated with, coated with, or otherwise configured to contain and administer an anesthetic at the insertion and set placement locations to minimize user discomfort and the risk of complications associated with the use of infusion sets. To do so, the system and method provides steps for mixing at a step (22) at least two of a solvent, an anesthetic, and a lubricant, applying the mixed compound as a coating to at least one surface of the infusion set, patch pump, or an element thereof at a step (24), and then substantially removing the solvent after coating at a step (26) to provide at least one of an anesthetic layer and a lubricant layer upon the infusion set, patch pump, or an element thereof.

8 Claims, 1 Drawing Sheet

(56) References Cited

U.S. PATENT DOCUMENTS

| | | | |
|---|---|---|---|
| 5,226,427 A | 7/1993 | Buckberg et al. | |
| 5,417,671 A | 5/1995 | Jackson | |
| 5,474,181 A | 12/1995 | Shillington et al. | |
| 5,582,599 A | 12/1996 | Daneshvar | |
| 5,797,882 A | 8/1998 | Purdy et al. | |
| 5,925,017 A | 7/1999 | Kriesel et al. | |
| 6,017,328 A | 1/2000 | Fischell et al. | |
| 6,461,644 B1 | 10/2002 | Jackson et al. | |
| 6,475,196 B1 | 11/2002 | Vachon | |
| 6,736,797 B1 | 5/2004 | Larsen et al. | |
| 6,749,588 B1 | 6/2004 | Howell et al. | |
| 7,207,974 B2 | 4/2007 | Safabash et al. | |
| 7,229,420 B2 * | 6/2007 | Sakai | A61M 1/0058 600/573 |
| 7,883,488 B2 * | 2/2011 | Shantha et al. | 604/22 |
| 7,981,085 B2 | 7/2011 | Ethelfeld | |
| 8,628,475 B2 * | 1/2014 | Wang | 600/458 |
| 2002/0156434 A1 | 10/2002 | Van Antwerp et al. | |
| 2003/0236552 A1 * | 12/2003 | Roby | 606/223 |
| 2005/0137498 A1 * | 6/2005 | Sakai | A61M 1/0058 600/562 |
| 2007/0021729 A1 | 1/2007 | Mogensen et al. | |
| 2007/0035042 A1 * | 2/2007 | Sakai | A61M 1/0058 261/19 |
| 2007/0299409 A1 | 12/2007 | Whitbourne et al. | |
| 2008/0295960 A1 | 12/2008 | Schalau, II et al. | |
| 2010/0106088 A1 * | 4/2010 | Yodfat et al. | 604/112 |

FOREIGN PATENT DOCUMENTS

| | | |
|---|---|---|
| WO | WO 97/41917 A1 | 11/1997 |
| WO | WO 99/03526 A1 | 1/1999 |
| WO | WO 2007/010522 A1 | 1/2007 |
| WO | WO 2009/001347 A1 | 12/2008 |
| WO | WO 2010-080715 A1 | 7/2010 |
| WO | WO 2010-085338 A1 | 7/2010 |

OTHER PUBLICATIONS

Roche, "The Professional's Pocket Guide to Infusion Site Management", 2007, pp. 1-47, Roche, USA. http://www.accu-chekinsulinpumps.com/documents/ProfessionalsPocketGuidetoInfusionSiteManagement.pdf.

* cited by examiner

INFUSION SET WITH ANESTHETIC COMPOUND

CROSS-REFERENCE TO RELATED APPLICATIONS

This application claims the benefit under 35 U.S.C. §119 (e) of U.S. Provisional Patent Application No. 61/202,079, entitled "Infusion Set With Anesthetic Compound", filed on Jan. 27, 2009, the entire content, disclosure and subject matter of said application being expressly incorporated herein by reference.

FIELD OF THE INVENTION

The present invention relates generally to components and elements of infusion sets, including one or more set elements which can be impregnated with, coated with, or otherwise configured to administer an anesthetic to minimize the risk of complications associated with the use of infusion sets, while maintaining a degree of comfort to the user.

BACKGROUND OF THE INVENTION

A large number of people, such as those suffering from conditions such as diabetes, use some form of injection or infusion therapy, such as daily insulin injections, to maintain close control of their glucose levels. Currently, in the insulin treatment example, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness. More recently, patch pumps have been developed to provide users with the advantages of insulin pumps but without the need for separate infusion sets and tubing connectors.

As interest in intensive therapy increases, users typically look to insulin pumps and patch pumps for improvements in the management of their condition. Therefore, interest in better pump-related therapy is on the rise. In this and similar examples, what is needed to fully meet this increased interest are advanced, improved, and novel new components and elements of current and future insulin infusion sets, including features and elements to minimize the risk of complications associated with the use of infusion sets, while maintaining a degree of comfort to the user.

Existing infusion sets, such as those used with insulin infusion pumps, are typically used for no more than 72 hours due to local site irritation and the risk of infection. To minimize such risks, anti-microbial and/or anti-inflammatory drugs can be used. For example, U.S. Patent Publication No. 2007/0299409 of Whitbourne et al. describes the use of anti-microbial and anti-inflammatory drugs to reduce complications associated with the use of infusion sets. However, these measures alone cannot fully eliminate patient discomfort during use of the infusion set.

Accordingly, a need exists for advanced, improved, and novel new components and elements of current and future insulin infusion sets and patch pumps, that further provide one or more set elements which can be impregnated with, coated with, or otherwise configured to apply or administer an anesthetic to minimize the risk of complications associated with the use of infusion sets, while maintaining a degree of comfort to the user.

SUMMARY OF THE INVENTION

An object of the present invention is to substantially address the above and other concerns, and provide advanced, improved, and novel new components and elements of current and future insulin infusion sets and patch pumps, that further provide one or more set elements which can be impregnated with, coated with, or otherwise configured to apply or administer an anesthetic to minimize the risk of complications associated with the use of infusion sets and patch pumps, while maintaining a degree of comfort to the user.

Another object of the present invention is to provide an exemplary hub, needle and/or catheter which can be impregnated with, coated with, or otherwise configured to apply or administer an anesthetic to minimize the risk of complications associated with the use of infusion sets, while maintaining a degree of comfort to the user.

Another object of the present invention is to provide an exemplary adhesive for use with the hub, which can be impregnated with, coated with, or otherwise configured to apply or administer an anesthetic to minimize the risk of complications associated with the use of infusion sets, while maintaining a degree of comfort to the user.

Another object of the present invention is to provide such elements which can be impregnated with, coated with, or otherwise configured to apply or administer an anesthetic for a desired period of time, such as for the entire expected life of the set, or for a shorter period.

Another object of the present invention is to provide an exemplary polymer catheter material which can be impregnated with, coated with, or otherwise configured to apply or administer an anesthetic.

Another object of the present invention is to provide an exemplary infusion set tubing material which can be impregnated with, coated with, or otherwise configured to apply or administer an anesthetic.

Another object of the present invention is to provide an exemplary cannula and/or catheter lubricant material which can be impregnated with, coated with, or otherwise configured to apply or administer an anesthetic.

Another object of the present invention is to provide an exemplary hub adhesive material which can be impregnated with, coated with, or otherwise configured to apply or administer an anesthetic.

Another object of the present invention is to provide an exemplary polymer coating material which can be impregnated with, coated with, or otherwise configured to dissolve over a period of time to apply or administer an anesthetic.

Another object of the present invention is to provide an exemplary metal, ceramic or composite matrix cannula which can be impregnated with, coated with, or otherwise configured to apply or administer an anesthetic.

Another object of the present invention is to provide the one or more elements which can be impregnated with, coated with, or otherwise configured to apply or administer an anesthetic wherein the anesthetic can be any one or more of amino esters (such as benzocaine), amino amides (such as lidocaine and/or prilocaine), or other anesthetic compounds.

Another object of the present invention is to provide one or more elements which can be impregnated with, coated with, or otherwise configured to apply or administer an anesthetic and which can be used in combination with anti-microbial and/or anti-inflammatory drugs.

Another object of the present invention is to provide one or more elements which can be impregnated with, coated with, or otherwise configured to apply or administer an anesthetic and which can be used in combination with anti-microbial and/or anti-inflammatory drugs, wherein the anti-microbial, anti-inflammatory, and anesthetic agents can be applied to wetted portions of the infusion set or included in the bulk polymer materials forming each article.

These and other objects are substantially achieved by providing an infusion set, that further provides one or more set elements including the hub, hub adhesive, fluid line tubeset, connectors, catheters and insertion needles which can be impregnated with, coated with, or otherwise configured to apply or administer an anesthetic to minimize the risk of complications associated with the use of infusion sets and to increase user comfort. In addition to these elements of infusion sets as they exist today, still other functional parts and/or components that exist in patch pumps, such as tubing, reservoirs, flexible reservoirs, cannula, etc., can also be impregnated with, coated with, or otherwise configured to apply or administer an anesthetic to minimize the risk of complications associated with the use of infusion sets and to increase user comfort.

These and other objects are also substantially achieved by providing a method for manufacturing and using an infusion set and/or one or more set elements which can be impregnated with, coated with, or otherwise configured to apply or administer an anesthetic to minimize the risk of complications associated with the use of infusion sets and to increase user comfort, wherein one or more elements can be provided with or manufactured with an anesthetic, such as an anesthetic within the polydialkylsiloxane lubricant formulation. Polydialkylsiloxanes can be applied after dissolution in organic solvents, such as aliphatic hydrocarbons, methylene chloride, or other chlorinated solvents. The anesthetic can be included in the formulation by dissolution in the solvent/polydialkylsiloxane mixture. The infusion set element(s) can then be coated with the lubricant/anesthetic/solvent mixture by dipping, spraying, inkjet printing, or similar methods. After evaporation of the solvent, a layer of the polydialkylsiloxane/anesthetic mixture remains on the surface of the element or device. The anesthetic can also be applied after mixing with an aqueous or bioerodible polymer formulation which is then applied to the surface of the element or device through any of the application methods described above. Still further, the anesthetic can be compounded into the polymer used to form any of the components described above.

BRIEF DESCRIPTION OF THE DRAWINGS

The various objects, advantages and novel features of the preferred embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

Figure 1:
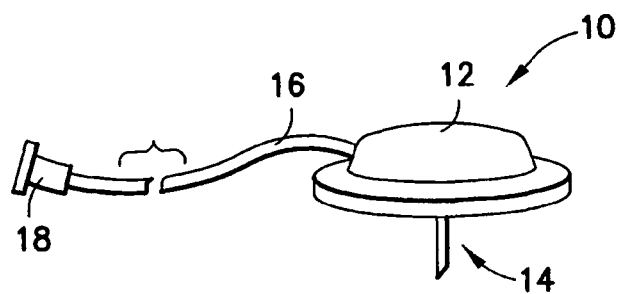
FIG. 1 is a perspective view of an infusion set which can include one or more exemplary elements in accordance with an embodiment of the present invention.

The embodiments of the present device described below illustrate a number of advanced, improved, and novel new components and elements of current and future insulin infusion sets, that further provide simplicity in manufacture and use improvements for both insulin and non-insulin applications. Exemplary embodiments are presented in separate descriptions, although the individual features of these embodiments can be combined in any number of ways to meet the needs of the user.

As will be appreciated by one skilled in the art, there are numerous ways of carrying out the examples, improvements and arrangements of infusion devices disclosed herein. Although reference will be made to the embodiments depicted in the drawings and the following descriptions, the embodiments disclosed herein are not meant to be exhaustive of the various alternative designs and embodiments that are encompassed by the disclosed invention.

The embodiments of the present device described below illustrate a number of features and elements of an insulin infusion set, including one or more set elements which can be impregnated with, coated with, or otherwise configured to apply or administer an anesthetic to minimize the risk of complications associated with the use of infusion sets, while maintaining a degree of comfort to the user. A collection of exemplary elements is shown by way of example in FIG. 1 which serves to introduce the embodiments of the present invention described in greater detail below. FIG. 1 illustrates an exemplary infusion set 10 including the following features. As shown in FIG. 1, the exemplary infusion set 10 can comprise a hub 12, a flexible catheter 14, a fluid line tubeset 16 and a pump connector 18. Additional infusion set elements are omitted for clarity. In the following description, a number of exemplary embodiments of set elements are described in greater detail, which can be provided for use with the exemplary infusion set 10. As noted above, one or more set elements can be impregnated with, coated with, or otherwise configured to apply or administer an anesthetic. A number of exemplary elements will now be described individually in greater detail.

As noted above, existing infusion sets, such as those used with insulin infusion pumps, are typically used for no more than 72 hours due to local site irritation and the risk of infection. To minimize such risks, anti-microbial and/or anti-inflammatory drugs can be used. However, these measures alone do not fully eliminate patient discomfort during use of the infusion set.

To resolve such issues associated with conventional infusion set construction, design and implementation, the present invention comprises elements of an infusion set for the delivery, or infusion, of insulin or other medications to the subcutaneous tissue of a user, in which one or more set elements can be impregnated with, coated with, or otherwise configured to apply or administer an anesthetic. The infusion set 10 typically comprises the hub 12 which includes the fixedly attached catheter 14, and the tubeset 16. The tubeset 16 connects the hub 12 to an infusion pump or other insulin supply (not shown) via a connector 18. In doing so, the tubeset 16 provides for fluid communication between the infusion pump reservoir and the hub 12.

The hub 12 can be affixed to a patient's skin surface (not shown) using an adhesive disposed on a lower surface of the hub. As shown in FIG. 1, the catheter 14 preferably protrudes from the lower surface of the hub 12 at a substantially perpendicular angle, although embodiments of the present invention are not limited thereto. For example, angled infusion sets are known and may be used in the practice of the present invention. As described in greater detail below, the infusion set can be configured as a disposable drug infusion set that releases an anesthetic at the infusion site to improve user comfort. The anesthetic can be released from the needle or from catheter surfaces, catheter materials or otherwise, as well as from the adhesive materials used to attach the infusion set to the user's skin.

In a first exemplary embodiment of the present invention, the catheter 14 material, such as a polymer or similar material, can be impregnated with or have embedded therein, coated with, or otherwise configured to contain and apply or administer the anesthetic or other materials. The first exemplary embodiment of the present invention can be expanded to include the fluid line tubeset 16, which can also be impregnated with or have embedded therein, coated with, or otherwise configured to contain and apply or administer the anesthetic or other materials. In the case of the tubeset, further design configurations can be provided to limit the anesthetic or other materials to an interior of the tubeset.

The first exemplary embodiment of the present invention can be expanded to include a cannula and/or catheter 14 lubricant material which can be impregnated with or have embedded therein, coated with, or otherwise configured to contain and apply or administer the anesthetic or other materials. Exemplary lubricant materials can comprise a solvent applied mixture of polydialkylsiloxanes and related compounds that are applied to an exterior of the catheter 14 and/or insertion needle or insertion device (not shown).

The first exemplary embodiment of the present invention can be expanded to include the hub 12 adhesive material(s) which can be impregnated with or have embedded therein, coated with, or otherwise configured to contain and apply or administer the anesthetic or other materials. As known to those skilled in the art, the placement of the set upon the user's skin surface typically involves an adhesive material to secure the set upon the insertion site for the duration of the set life. In doing so, the adhesive material typically contacts the skin surface at or near the insertion site, and therefore, provides a medium to contain and apply or administer the anesthetic or other materials as desired.

The first exemplary embodiment of the present invention can be expanded to include a polymer coating material on the catheter 14 and/or insertion device or needle (not shown) which can be impregnated with or have embedded therein, coated with, or otherwise configured to contain the anesthetic or other materials, and then dissolve over a period of time to apply or administer the anesthetic or other materials. The anesthetic or other materials can be embedded in such a biocompatible polymer coating, such as a hydrogel, which is disposed on at least a portion of the catheter 14 and/or the insertion device or needle (not shown). In doing so, the coating can be configured to dissolve over a period of time to release the active ingredients of the anesthetic or other materials over the useful life of the infusion set, or for any shorter period thereof.

The first exemplary embodiment of the present invention can be expanded to include a rigid cannula (not shown) that serves the same function as the flexible catheter 14. The rigid cannula can be comprised of any suitable metal, ceramic or composite matrix cannula which can be impregnated with or have embedded therein, coated with, or otherwise configured to contain and apply or administer the anesthetic or other materials while serving the same function as the catheter 14.

In each of the exemplary embodiments of the present invention, the anesthetic which can be impregnated or embedded in and released by the infusion set and set elements can be any one or more of amino esters (such as benzocaine), amino amides (such as lidocaine and/or prilocaine), or other anesthetic compounds. Further, each of the exemplary embodiments of the present invention described above can be used in combination with anti-microbial and/or anti-inflammatory drugs. Such anti-microbial, anti-inflammatory, and anesthetic agents can be applied to wetted portions of the infusion set, such as the infusion set tubing 16 and connectors 18, or can be included in the bulk polymer materials forming each article or set element.

In each of the exemplary embodiments of the present invention, the rate at which the anesthetic is released from the device can be configured such that it will provide the desired benefits for at least the entire expected use of the set, or for a shorter period, such as a short period over which a user is becoming comfortable with the set, or any variation in between.

As described above, an insulin infusion set can include one or more set elements including a hub, hub adhesive, fluid line tubeset, connectors, catheters and insertion needles which can be impregnated with, have embedded therein, be coated with, or otherwise configured to administer an anesthetic to minimize the risk of complications associated with the use of infusion sets and increase user comfort. By using the infusion set to deliver an anesthetic directly to the infusion site, and optionally in combination with one or more of an anti-microbial, anti-inflammatory and antibiotic agent, the user's or patient's discomfort can be reduced during the use of the infusion set. The useful life of the infusion set can also be increased.

Through the selection and use of one or more of the infusions set elements described above, select locations of the embedded drug can be chosen to permit drug delivery closer to the area of concern, such as through the use of the adhesive patch that is in contact with the skin, the cannula lubricant touching the subcutaneous tissue and the entry through the skin, since drugs released from the tubing or inner walls of the cannula is more likely to perfuse in the tissue.

Figure 2:
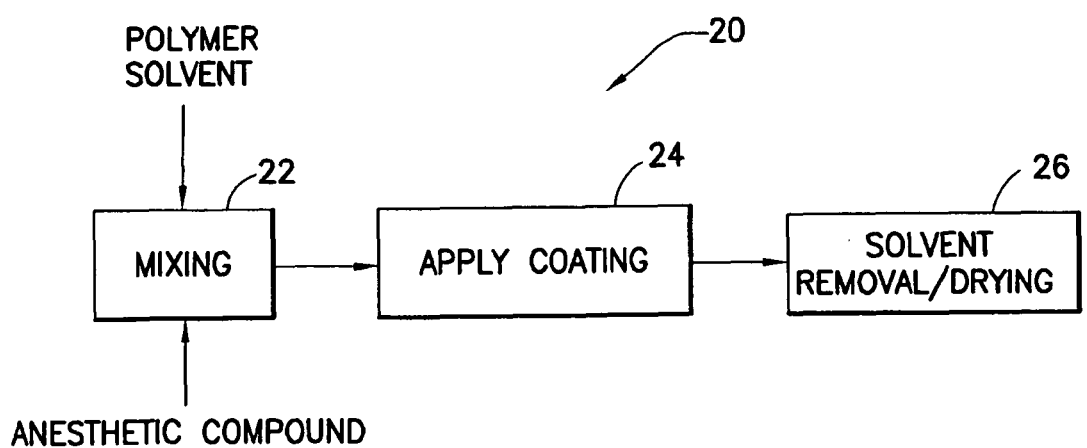
FIG. 2 is a flow chart illustrating exemplary manufacturing steps for impregnating, coating or otherwise configuring the elements to apply or administer the anesthetic.

FIG. 2 is a flow chart illustrating exemplary manufacturing steps 20 for impregnating, coating or otherwise configuring the elements to apply or administer the anesthetic. An exemplary coating process can be achieved though a minimal number of steps, consisting of spraying, dipping, or otherwise applying the solvent/lubricant/anesthetic formulation and allowing the solvent to evaporate from the device. For example, materials such a polymer solvent or similar material, can be mixed with an anesthetic compound or similar material in a first step 22. As noted above, the materials of step 22 can be used in the construction of the elements of the infusion set, or can be applied as a coating in a subsequent step 24. A finished product can then be achieved after solvent removal and/or after drying in step 26. Any of the exemplary steps shown can be combined to ease manufacture.

For example, one or more elements of the infusion set can be provided with or manufactured with an anesthetic, such as an anesthetic within the polydialkylsiloxane lubricant formulation. In one example, polydialkylsiloxanes can be applied after dissolution in organic solvents in step 22, such as aliphatic hydrocarbons, methylene chloride, or other chlorinated solvents. The anesthetic can be included in the formulation by dissolution in the solvent/polydialkylsiloxane mixture. The elements can then be coated with the lubricant/anesthetic/solvent mixture by dipping, spraying, inkjet printing, or similar methods in step 24. After evaporation of the solvent in step 26, a layer of the polydialkylsiloxane/anesthetic mixture remains on the surface of the element or device. The anesthetic can also be applied after mixing with an aqueous or bioerodible polymer formulation which is then applied to the surface of the element or device through any of the application methods described above. Still further, the anesthetic can be compounded into the polymer used to form any of the components described above.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and equivalents thereof.

What is claimed is:

1. An infusion set configured to apply or administer an anesthetic, comprising:
   a hub,
   a catheter connected to said hub, and
   an anesthetic coating comprising an anesthetic and a coating, the anesthetic coating disposed on at least one inner surface of said hub or catheter,
   wherein infusate flowing through said infusion set to a catheter insertion site contacts said at least one inner surface of said hub or catheter, and
   wherein said coating remains on said inner surface of said hub or catheter and releases the anesthetic to said infusate over a period of time during use of said infusion set.

2. An infusion set configured to apply or administer an anesthetic as claimed in claim 1, wherein said coating comprises a biocompatible polymer coating, such as a hydrogel.

3. An infusion set configured to apply or administer an anesthetic as claimed in claim 1, wherein a second anesthetic coating is provided as a skin-contacting, adhesive layer on an outer surface of said hub.

4. An infusion set configured to apply or administer an anesthetic as claimed in claim 1, wherein an anesthetic is provided as part of a construction material of said hub or catheter.

5. An infusion set configured to apply or administer an anesthetic as claimed in claim 1, wherein said coating comprises a polydialkylsiloxane lubricant.

6. An infusion set configured to apply or administer an anesthetic as claimed in claim 1, wherein said anesthetic comprises at least one of amino esters and amino amides.

7. An infusion set configured to apply or administer an anesthetic as claimed in claim 1, wherein at least one surface of said hub or catheter is provided with an anesthetic combined with at least one of a lubricant material, an anti-microbial material, and an anti-inflammatory material.

8. An infusion set configured to apply or administer an anesthetic as claimed in claim 1, wherein said infusion set further comprises a fluid tube set having at least one surface provided with an anesthetic combined with at least one of a lubricant material, an anti-microbial material, and an anti-inflammatory material.

* * * * *